US008753836B2

(12) United States Patent
Freeland et al.

(10) Patent No.: US 8,753,836 B2
(45) Date of Patent: Jun. 17, 2014

(54) DEWAXING BUFFER CONTAINING A WATER-SOLUBLE ORGANIC SOLVENT AND METHODS OF USE THEREOF

(75) Inventors: Jennifer H. Freeland, Portage, MI (US); Marsha A. Harvey, Scotts, MI (US)

(73) Assignee: Richard-Allan Scientific Company, Kalamazoo, MI (US)

( * ) Notice: Subject to any disclaimer, the term of this patent is extended or adjusted under 35 U.S.C. 154(b) by 10 days.

(21) Appl. No.: 13/356,491

(22) Filed: Jan. 23, 2012

(65) Prior Publication Data

US 2013/0189730 A1 Jul. 25, 2013

(51) Int. Cl.
*G01N 1/30* (2006.01)
*G01N 1/36* (2006.01)

(52) U.S. Cl.
USPC ............. 435/40.52; 436/17; 436/18; 436/63; 436/175; 436/177; 435/40.5; 435/7.1; 435/7.21

(58) Field of Classification Search
CPC ............. C07D 307/12; C07D 307/06; C08G 2650/28; C08G 2650/58; C08G 65/02; G01N 1/30; G01N 1/36; G01N 2001/305; G01N 2001/36; A01N 1/02; A01N 1/021; A01N 1/00; A01N 1/0205
See application file for complete search history.

(56) References Cited

U.S. PATENT DOCUMENTS

| | | | | |
|---|---|---|---|---|
| 4,366,002 A * | 12/1982 | Carandang | ........................ | 134/2 |
| 5,259,993 A * | 11/1993 | Short | ............................. | 510/203 |
| 6,130,195 A * | 10/2000 | Doyel et al. | .................. | 510/365 |
| 6,544,798 B1 | 4/2003 | Christensen et al. | | |
| 6,649,368 B1 | 11/2003 | Aghassi et al. | | |
| 6,855,552 B2 | 2/2005 | Towne et al. | | |
| 6,855,559 B1 | 2/2005 | Christensen et al. | | |
| 7,067,325 B2 | 6/2006 | Christensen et al. | | |
| 7,410,753 B2 | 8/2008 | Hopkins et al. | | |
| 7,550,298 B2 | 6/2009 | Towne et al. | | |
| 2003/0100043 A1 | 5/2003 | Kalra et al. | | |
| 2003/0175852 A1 | 9/2003 | Kalra et al. | | |
| 2004/0126399 A1 | 7/2004 | Zhang et al. | | |
| 2008/0261266 A1 | 10/2008 | Kram et al. | | |
| 2009/0155907 A1 | 6/2009 | Winther et al. | | |
| 2009/0246824 A1 * | 10/2009 | Wiederhold et al. | ........ | 435/40.52 |
| 2010/0152086 A1 * | 6/2010 | Wu et al. | ........................ | 510/175 |

OTHER PUBLICATIONS

Saravanakumar Shanmuganathan, Dessy Natalia, Anne van den Wittenboer, Christina Kohlmann, Lasse Greiner and Pablo Dominguez de Maria, Enzyme-catalyzed C—C bond formation using 2-methyltetrahydrofuran (2-MTHF) as (co)solvent: efficient and bio-based alternative to DMSO and MTBE, 2010, Green Chem., 2010, 12, 2240-2245, published online Nov. 9, 2010.*

* cited by examiner

*Primary Examiner* — Blaine Lankford
*Assistant Examiner* — Trent R Clarke
(74) *Attorney, Agent, or Firm* — Workman Nydegger

(57) ABSTRACT

Dewaxing buffers containing a water-soluble organic solvent, methods for use thereof, and kits incorporating dewaxing buffers. The dewaxing buffers contain a water soluble organic solvent that has a boiling point of at least 80° C. The dewaxing buffers described herein can be used to quickly and efficiently remove embedding paraffin from slide-mounted tissue sections in an aqueous buffer solution at elevated temperature without fear of paraffin redeposition of the slides. In addition, the dewaxing buffers described herein can be used to perform dewaxing and HIER in a single step, which can substantially reduce protocol time and lower the risk of sample loss or damage.

9 Claims, No Drawings

DEWAXING BUFFER CONTAINING A WATER-SOLUBLE ORGANIC SOLVENT AND METHODS OF USE THEREOF

BACKGROUND

Paraffin has long been used as an embedding medium in the preparation of tissue specimens for histological studies. In some instances, plastic resins have also been used as embedding medium. Such embedding processes generally include the steps of specimen fixation (e.g., formalin fixation), dehydration, clearing, paraffin infiltration or impregnation, blocking or embedding in a block of paraffin, slicing the block and specimen into thin sections, mounting the sections on slides, removing the paraffin and solvents employed for this purpose (i.e., dewaxing or deparaffinizing), and staining the sections prior to microscopic analysis. The primary purpose of the embedding medium is to permit the specimens to be sectioned and mounted in the natural state. Paraffin-embedding has the advantage that the wax can be dissolved away from specimens prior to staining, allowing sections to be stained as bare tissue and avoiding the extra difficulties associated with the presence of resin-based embedding medium, which is more difficult to remove.

Recent improvements in paraffin-embedding compositions have broadened its applicability while maintaining its compatibility with downstream preparation and analysis of samples. Consequently, dewaxing of fixed, paraffin-embedded tissue sections is still a widely used methodology, particularly in hospital histopathology laboratories for immuno-diagnostic purposes.

One method commonly employed for dewaxing involves the dissolution of the embedding paraffin in organic solvents. For example, xylene, which is a flammable, volatile and toxic organic solvent, is currently commonly used in protocols to solubilize paraffin for dewaxing of specimen sections. Typically, the microscope slide-mounted specimen is immersed in a xylene bath until the paraffin is dissolved.

Another method commonly employed for dewaxing involves the melting and removal of embedding paraffin in a heated bath containing an aqueous buffer solution. The use of heated buffer solution has the additional advantage that it allows antigen retrieval through a process known as heat-induced epitope retrieval ("HIER"). HIER is a pretreatment procedure often used prior to immunohistochemistry ("IHC") or in-situ hybridization ("ISH") procedures to improve staining by heat-induced modification of the molecular conformation of target proteins contained in slide-mounted specimen material. Typically, this modification process is necessary because, although aldehyde-based fixatives (e.g., formalin) are excellent for preserving cellular morphology, they also cause protein cross-linking, resulting in the inability of some protein epitopes to bind complementary antibodies. HIER is commonly used in conjunction with enzyme digestion as a means of improving the reactivity of various antigens within IHC/ISH staining reactions.

Existing buffer formulations that are configured to simultaneously dewax slides and perform HIER prior to IHC/ISH utilize small concentrations of surfactants and other emulsifiers to break up paraffin. The HIER procedure places slides at an elevated temperature (e.g., from 70 to 100° C.), allowing paraffin to melt and surfactants to gently lift paraffin to the buffer surface. However, known buffer formulations and methods have limited performance, sometimes creating paraffin streaking, slide recoating, and inconsistent staining results.

Accordingly, there is a need for dewaxing compositions and methods that can effectively remove paraffin or improved paraffin-based embedding materials from specimens prior to immunohistochemical or other diagnostic analyses, while minimizing danger to users, allowing compatibility with automated systems, and maintaining compatibility with downstream analyses. Dewaxing compositions and methods that entail no or limited toxicity or carcinogenicity, produce no or minimal odors, reduce the quantity of toxic solvents used, minimize hazardous wastes, and/or decrease corrosiveness and flammability are needed.

BRIEF SUMMARY

Disclosed herein are dewaxing buffers containing a water-soluble organic solvent, methods for use thereof, and kits incorporating dewaxing buffers. The dewaxing buffers described herein can be used to quickly and efficiently remove embedding paraffin from slide-mounted tissue sections in an aqueous buffer solution at elevated temperature without fear of paraffin redeposition of the slides. In addition, the dewaxing buffers described herein can be used to perform dewaxing and HIER in a single step, which can substantially reduce protocol time and lower the risk of sample loss or damage.

In one embodiment, a dewaxing buffer includes a buffering agent, an organic solvent having a boiling point greater than 80° C. and having a solubility in water of at least 20 volume % ("vol %"), and water. A working solution of the dewaxing buffer may include greater than 95 vol % of water. In one embodiment, the dewaxing buffer working solution may be prepared from a concentrated dewaxing buffer reagent by dilution of the concentrated solution with water.

In one aspect, the dewaxing buffer is capable of solublizing melted embedding paraffin in aqueous solution at elevated temperature and the melted paraffin does not re-solidify upon cooling. Likewise, the dewaxing buffer is capable of lowering the melting point of paraffin, which can substantially reduce protocol time. It is believed that this activity is due to the action of the water soluble organic solvent. That is, due to the duplicity of the solvent's chemical nature, it is believed that the solvent has the capability to disrupt the hydrogen-bonding in aqueous solutions, as well as dissolve or solublize organic molecules such as paraffin in water.

These and other objects and features of the present invention will become more fully apparent from the following description and appended claims, or may be learned by the practice of the invention as set forth hereinafter.

DETAILED DESCRIPTION

I. Introduction

Disclosed herein are dewaxing buffers containing a water-soluble organic solvent, methods for use thereof, and kits incorporating dewaxing buffers. The dewaxing buffers described herein can be used to quickly and efficiently remove embedding paraffin from slide-mounted tissue sections in an aqueous buffer solution at elevated temperature. The dewaxing buffers described herein are capable of solublizing melted embedding paraffin, which means that slide can be removed from the dewaxing buffer without fear of paraffin redeposition of the slides. The dewaxing buffers described herein are capable of lowering the melting point of paraffin, which can substantially reduce protocol time. Likewise, because the slide-mounted tissue samples are dewaxed in aqueous solution, it is not necessary to dehydrate the tissue samples prior to dewaxing. This can also substantially reduce slide processing time. In addition, the dewaxing buffers described herein can be used to perform dewaxing and HIER in a single step, which can substantially reduce protocol time and lower the risk of sample loss.

II. Dewaxing Buffers

In one embodiment, a dewaxing buffer is described. The dewaxing buffer may include a buffering agent, an organic solvent having a boiling point greater than 80° C. and having a solubility in water of at least 20 volume % ("vol %"), and water. In one embodiment, the dewaxing buffer has a pH in a range from about pH 5 to about pH 10 or a pH in a range from about pH 6 to about pH 9. Generally, however, any pH can be chosen depending on the pH preferred for a particular tissue type or a particular dewaxing protocol.

In one embodiment, the dewaxing buffer is capable of dissolving or solublizing organic molecules such as paraffin in water. It is believed that the organic solvent is primarily responsible for this property. Nevertheless, as will be discussed in greater detail herein, the component of the dewaxing buffer work synergistically to stabilize cell structure during and after dewaxing, to effectively and completely remove embedding wax from slide mounted tissue samples, to prevent redeposition of embedding wax on slides, and to stabilize cell structure during and after dewaxing.

In one embodiment, the organic solvent has a boiling point of at least 90° C., at least 100° C., at least 110° C., at least 120° C., at least 130° C., at least 140° C., at least 150° C., at least 160° C., at least 170° C., at least 180° C., at least 190° C., or at least 200° C. In general, however, higher boiling solvents (e.g., solvents having a boiling point above 110° C.) are preferred over lower boiling solvents (e.g., solvents having a boiling point below about 75° C.). For example, some HIER protocols require incubating slides in dewaxing buffer at elevated temperature (e.g., above 80° C.) for about 1-20 hours. In such situations, higher boiling solvents are less likely to evaporate out of the buffer, which, if it occurs, would reduce the capability of the buffer to solublize wax over time. Likewise, higher boiling solvents are preferred because they are less likely to contribute to solvent odors from the buffer due to the fact that they do not readily evaporate.

In one embodiment, a working solution of the dewaxing buffer may include a lower amount of the organic solvent of about 0.1 vol %, 0.2 vol %, 0.25 vol %, 0.3 vol %, or 0.4 vol %, an upper amount of the organic solvent of about 5 vol %, 3 vol %, 2 vol %, 1 vol %, or 0.5 vol %, or any combination of the recited lower and amounts. In a preferred embodiment, the buffer includes about 0.25 vol % of the organic solvent. Dewaxing buffers described herein having organic solvent amounts as low as 0.1 vol % to 0.25 vol % are able to solubilize substantial amounts of embedding wax from slide mounted tissue samples. It is submitted that it is surprising and unexpected that such small amounts of organic solvent can be used to solubilize embedding wax in aqueous solution.

In one embodiment, the organic solvent may have a lower range of solubility in water of about 20 vol %, 25 vol %, 30 vol %, 35 vol %, 40 vol %, 45 vol %, or 50 vol %, an upper range of solubility in water 99 vol %, 95 vol %, 90 vol %, 85 vol %, 80 vol %, 75 vol %, 70 vol %, 65 vol %, 60 vol %, 55 vol %, 50 vol %, or any combination of the recited lower and upper solubility limits. In a preferred embodiment, the organic solvent is miscible in water (i.e., the solvent and water can be combined in any proportion).

In one embodiment, suitable examples of organic solvents having the above described properties that may be included in the dewaxing buffer include, but are not limited to, aliphatic, alcohol, aldehyde, ketone, and ester derivatives of heterocyclic organic compounds such as oxetane, furan, tetrahydrofuran, pyran, tetrahydropyran, thietane, thiophene, tetrahydrothiophene, thiopyran, or tetrahydrothiopyran. For example, known derivatives of tetrahydrofuran, which is also referred to as oxolane, include, but are not limited to methyl tetrahydrofuran, tetrahydrofuryl alcohol, 2-(hydroxymethyl) oxolan-3-ol, glycofural (2-((Tetrahydrofurfuryl)oxy)ethanol), 2-(hydroxymethyl)oxolane-3,4-diol, bishydroxymethyl-tetrahydrofuran, methyl tetrahydrofuran carboxylate, and the like. Other derivatives of the above listed compounds include, but are not limited to, tetrahydrothiophenyl methanol, tetrahydropyranyl methanol, (oxetanyloxy)methanol, and furanol.

In another embodiment, the organic solvent may be at least one of furfural, furfuryl alcohol, methyl tetrahydrofuran, tetrahydrofuryl alcohol, diglyme, diethylene glycol, dimethylformamide, dimethyl sulfoxide, dioxane, diethanolamine, propylene glycol, or a derivative thereof.

In a preferred embodiment, the organic solvent is tetrahydrofuryl alcohol ("THFA"). THFA has a boiling point of about 178° C., which means it will not readily evaporate it is miscible in water, it has very little odor, it is non reactive, and it has a low order of toxicity, and it is readily biodegradable. In addition, THFA is derived from agricultural products such as corn cobs and sugar cane bagasse and it is not a product of petroleum distillation. In another preferred embodiment, the organic solvent is methyl tetrahydrofuran ("me-THF"). me-THF has many properties in common with THFA except that me-THF has a boiling point of about 78-80° C. The structures of THFA and me-THF are shown below at Formulas 1 and 2, respectively.

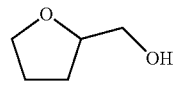

Formula 1-THFA

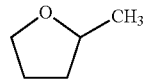

Formula 2-me-THF

In one embodiment, the dewaxing buffer may further include about 0.5 vol % to about 2 vol % of a polyfunctional alcohol. Suitable examples of polyfunctional alcohols include, but are not limited to, polyethylene glycol ("PEG"), a polypropylene glycol ("PPG"), sugar alcohols, and combinations thereof. Polyfunctional alcohols, such as PEG, can alter the activity of water by changing and/or disrupting the normal hydrogen boding structure of water. In the present case, the inventors have discovered that PEG can help solubilized wax to form crystalline structures and flocculate as the dewaxing solution cools, which can help to prevent redeposition of embedding wax on the slides. In addition, PEG can help to stabilize cellular structure in the tissue samples, which can lead to better and more consistent staining and better cell morphology.

PEGs are oligomers or polymers of ethylene oxide and are prepared by polymerization of ethylene oxide. PEGs are commercially available over a wide range of molecular weights from about 200 g/mol to about 10,000,000 g/mol. PEGs are readily soluble in water and most alcohols and are generally stable in acidic and basic solution. The basic structure of PEGs is represented below at Formula 3.

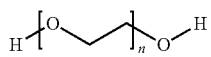

Formula 3

In PEGs, n can be as low as about 4 for PEG 200 or in the hundreds of thousands for very high molecular weight PEGs. PEGs are generally liquid up to a molecular weight of about 600 daltons; PEGs having average molecular weights above about 600 daltons are generally solid at room temperature. PEGs are typically designated according to the average molecular weight of the polymer. For example, PEG 200 is a polymer having an average molecular weight of 200 daltons, PEG 500 is a polymer having an average molecular weight of 500 daltons, PEG 1000 is a polymer having an average molecular weight of 1000 daltons, and so on. In some nomenclature systems, PEGs are also classified according to the value of n. For example, PEG 200 is often referred to as PEG 4, PEG 500 is often referred to as PEG 10, PEG 1000 is often referred to as PEG 20, and so on.

Suitable examples of PEGs that may be used herein include liquid PEGs such as PEG 200, PEG 300, PEG 400, PEG 500, and PEG 600 and solid PEGs such as PEG 1000, PEG 2000, PEG 5000, PEG 10,000, PEG 15,000, and the like. Solid PEGs, which are readily soluble in water, can be made into aqueous solutions (e.g., 50% weight/volume solutions) that can be added to the dewaxing buffer solution. In a preferred embodiment, the PEG is selected from the group consisting of PEG 200, PEG 300, PEG 400, PEG 500, PEG 600, and combinations thereof. In a more preferred embodiment, the PEG is PEG 200.

PPG (aka polypropylene oxide) is a polymer of propylene glycol. PPG has many properties in common with polyethylene glycol. However, solubility in water decreases rapidly with increasing molar mass. Secondary hydroxyl groups in PPG are less reactive than primary hydroxyl groups in polyethylene glycol. PPG is generally less toxic than PEG. The basic structure of PEGs is represented below at Formula 4.

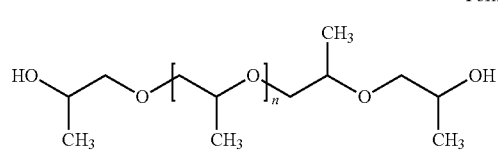

Formula 4

Sugar alcohols have the general formula $H(HCHO)_{n+1}H$, whereas sugars have $H(HCHO)_nHCO$. Sugar alcohols are a hydrogenated form of carbohydrate, whose carbonyl group (aldehyde or ketone, reducing sugar) has been reduced to a primary or secondary hydroxyl group (hence the alcohol).

Some common sugar alcohols include, arabitol, xylitol, ribitol (5-carbon), mannitol, sorbitol (6-carbon), isomalt, maltitol, lactitol, and polyglycitol (12-carbon). Monosaccharides, disaccharides, and polysaccharides can form sugar alcohols; however, sugar alcohols derived from disaccharides and polysaccharaides (e.g., maltitol and lactitol) are not entirely hydrogenated.

In one embodiment, the dewaxing buffer may further include about 0.1 vol % to about 4 vol %, about 0.15 vol % to about 3 vol %, about 0.2 vol % to about 2 vol %, about 0.25 vol % to about 1 vol %, about 0.30 vol % to about 0.5 vol %, about 0.35 vol % to about 0.4 vol % of a surfactant. Preferably, the amount of surfactant in the dewaxing buffer is about 0.25 vol %. In some situation surfactant solutions having higher amounts of surfactant (e.g., higher than about 4%) may be able to effectively dewax slide mounted tissue samples and solublize the embedding paraffin. Nevertheless, the inventors have found that such high levels of surfactant are generally not recommended because they can solublize portions of the membranes of the cells in the tissue and create artifacts.

In one embodiment, suitable examples of surfactants that may be included in the dewaxing buffer include, but are not limited to, anionic surfactants, cationic surfactants, zwitterionic surfactants, nonionic surfactants, and combinations thereof. In a specific embodiment, the surfactant may be Triton X-100 (also known as octyl phenol ethoxylate) or Tween 20 (also known as polyoxyethylene (20) sorbitan monolaurate).

In one embodiment, the dewaxing buffer working solution described herein above may include greater than 95 vol %, greater than 96 vol %, or greater than 97 vol % of water.

In one embodiment, a concentrated dewaxing reagent is disclosed. The concentrated dewaxing reagent may include a buffering agent, an organic solvent having a boiling point greater than about 80° C. and having a solubility in water of at least 20 vol %, about 7.5 vol % to about 30 vol % of PEG 200, and at least 45 vol % to 50 vol % water, or, preferably, at least 47 vol % water. In one embodiment, the concentrated dewaxing reagent may further include about 3 vol % to about 15 vol % of a surfactant.

In one embodiment, the dewaxing buffer working solution described above may be prepared from the concentrated dewaxing buffer reagent by dilution of the concentrated solution with water. For example, 100 ml of the concentrated reagent may be diluted with 1400 ml of deionized water to make 1500 ml of dewaxing buffer working solution.

In one embodiment, the concentrated dewaxing reagent may be included in a kit that includes at least one container of the concentrated dewaxing reagent and a protocol that includes instructions for diluting the concentrated dewaxing reagent to make a dewaxing buffer working solution and a description of a method for dewaxing a slide-mounted tissue section in the dewaxing buffer.

In one embodiment, the kit may further include a first concentrated dewaxing reagent having a first buffering agent capable of buffering at about pH 6, a second concentrated dewaxing reagent having a second buffering agent capable of buffering at about pH 8, and a third concentrated dewaxing reagent having a third buffering agent capable of buffering at about pH 9. Each of the first, second, and third concentrated dewaxing reagents include the organic solvent, PEG 200, and water.

In one embodiment, the first concentrated dewaxing reagent includes a first coloring agent, the second concentrated dewaxing reagent includes a second coloring agent, and the third concentrated dewaxing reagent includes a third coloring agent, and wherein the first, second, and third coloring agent serve to provide an easy means to visually distinguish the first, second, and third concentrated dewaxing reagents from one another. For example, the first concentrated dewaxing reagent may include an orange color, the second concentrated dewaxing reagent may include a purple color, and the third concentrated dewaxing reagent may include a blue color. While such colors are selected to facilitate distinguishing between various buffer solutions, the coloring agents are also chosen to be inert and to not interfere with dewaxing and subsequent staining protocols.

III. Dewaxing Methods

In one embodiment, a dewaxing method is described. The method includes (1) providing slide-mounted tissue section, wherein the tissue section is at least partially embedded in an embedding paraffin and (2) immersing the slide-mounted tissue section in a dewaxing buffer that includes a buffering agent, an organic solvent having a boiling point greater than 80° C. and having a solubility in water of at least 20 volume % ("vol %"), and at least 95 vol % water. In one embodiment, the dewaxing buffer may further include at least one of a PEG or a surfactant.

The method further includes (3) incubating the slide-mounted tissue section in the dewaxing buffer at a selected temperature for a period of time sufficient for dewaxing the slide-mounted tissue section, (4) cooling the dewaxing buffer, and (5) removing the slide-mounted tissue section from the dewaxing buffer.

In one embodiment, the incubating further includes: (i) immersing the slide-mounted tissue section in the dewaxing buffer at about room-temperature, (ii) pre-heating the slide-mounted tissue section in the dewaxing buffer to about 85° C., (iii) raising the temperature of the dewaxing buffer having the slide-mounted tissue section immersed therein to about 97° C., (iv) allowing the slide-mounted tissue section to incubate at about 97° C. in the dewaxing buffer for 10 minutes to 24 hours, and (v) cooling the dewaxing buffer having the slide-mounted tissue section immersed therein to about 85° C.

In one embodiment, the dewaxing buffer is capable of lowering a melting point of the embedding paraffin by at least 5° C., at least 7° C., or at least 10° C. Without being tied to one theory, it is believed that the organic solvent is primarily responsible for lowering the melting point of the embedding paraffin. Such a lowering of the melting point of the embedding wax or paraffin can substantially reduce the time and energy needed to remove embedding wax from slide-mounted tissue samples.

In one embodiment, 100 ml of the dewaxing buffer is capable of solublizing at least 1 g to 5 g of paraffin in aqueous solution. It is respectfully submitted that it is surprising and unexpected that a dewaxing buffer containing only about 0.25 vol % of an organic solvent, for example, can solubilize such significant amounts of paraffin.

In one embodiment, the dewaxing buffer is capable of solublizing substantially all of the embedding paraffin from the slide-mounted tissue section at or above about 58-62° C. Likewise, the dewaxing buffer is capable of solublizing about 7-12% of the embedding paraffin from the slide-mounted tissue section at about 55° C. and about 5% of the embedding paraffin from the slide-mounted tissue section below 55° C.

When the buffers and the dewaxing/epitope retrieval methods described herein were tested on paraffin-embedded tissue samples, it was found that the buffers described herein could effectively dewax slide in aqueous solution without having to revert to the use of toxic and harsh organic solvents (e.g., xylene). And because the slides are being dewaxed in aqueous solution, it is not necessary to dehydrate the tissue samples prior to dewaxing, which is generally necessary when slides are dewaxed in xylene or a similar solvent. This can save a great deal of time relative to known protocols.

The dewaxing/epitope retrieval methods described herein were compared to standard buffers and methods. For example, dewaxing/epitope retrieval were tested and compared using standard citrate buffer, Dako Flex low pH, and a dewaxing buffer containing citrate buffer, 1.5 vol % PEG 200, 0.5 vol % Triton X100, 0.5 vol % THFA, and ~97 vol % DI water. It was observed that the tissues that were treated with the buffers/methods described herein were dewaxed at least as well and in many ways better than the dewaxing/epitope retrieval achieved with standard citrate buffer and Dako Flex low pH. Likewise, tissues treated with the buffers/methods described herein showed good cell morphology and were free of artifacts produced by ineffective wax removal or redeposition.

The dewaxing buffer can be heated for dewaxing and/or epitope recovery (e.g., HIER) using any means known in the art. Likewise, the buffers and method described herein are not tied to expensive and complicated automated instruments that can consume unnecessarily large quantities of buffer or risk sample loss or damage through harsh heating and washing protocols. For example, the buffer can be heated in a buffer tank called a PT Module, which is available from Lab Vision, Incorporated of Fremont, Calif. The PT Module is designed to provide standardization of manual steps associated with the pre-treatment of slides.

The PT Module is designed to simultaneously perform dewaxing and epitope recovery (i.e., HIER) on slides prior to immunostaining Slides are loaded into the PT Module and immersed in dewaxing buffer. The PT Module has an integrated computer for programming pre-treatment programs. The user may also modify the time and temperature settings to further optimize the results.

A typical PT module has a buffer tank that holds approximately 1500 ml of buffer and has a capacity for dewaxing 24 slides simultaneously. 1500 ml of the buffer described herein can be used in up to five to eight or, preferably, up to three separate dewaxing runs without exceeding the dewaxing capacity of the buffer. That is, it was found that 1500 ml of the buffer described herein can be used to dewax as many as 192 to 120 individual slides, or, preferably, about 72 slides without observing evidence of ineffective wax removal or wax redeposition.

In addition, in contrast to some methods known in the art that depend on processing slides one at a time on a horizontal tray with that dewax solely by floating paraffin on the top of aqueous solution (i.e., the paraffin is immiscible in the buffer), the buffers and methods described herein dewax by actually solublizing paraffin in aqueous solution. As such, slides can be processed in bulk in a vertical arrangement in heated buffer tanks without the need for complicated systems for removing melted wax from the surface of the solution. This combines the effectiveness of wax removal in solvents like xylene with the convenience of dewaxing in aqueous buffer.

IV. Examples

Example 1

Working Buffer Formulations

The formulations of several dewaxing buffer working solutions are shown below Tables 1-3.

TABLE 1

| Dewax Buffer - Low pH | | |
|---|---|---|
| Component | Volume (ml) | Percent |
| Citrate Buffer Concentrate | 0.5 | 0.98% |
| DI Water | 49.5 | 96.59% |
| PEG 200 | 0.75 | 1.46% |
| Triton X100 | 0.25 | 0.49% |
| THFA | 0.25 | 0.49% |
| Total | 51.25 | 100.00% |

TABLE 2

Dewax Buffer - Medium pH

| Component | Volume (ml) | Percent |
|---|---|---|
| EDTA-HEPES Buffer Concentrate | 0.5 | 0.98% |
| DI Water | 49.5 | 96.59% |
| PEG 200 | 0.75 | 1.46% |
| Triton X100 | 0.25 | 0.49% |
| THFA | 0.25 | 0.49% |
| Total | 51.25 | 100.00% |

TABLE 3

Dewax Buffer - High pH

| Component | Volume (ml) | Percent |
|---|---|---|
| Tris-EDTA Buffer Concentrate | 0.5 | 0.98% |
| DI Water | 49.5 | 96.59% |
| PEG 200 | 0.75 | 1.46% |
| Triton X100 | 0.25 | 0.49% |
| THFA | 0.25 | 0.49% |
| Total | 51.25 | 100.00% |

Example 2

Working Buffer Formulations

The formulations of several concentrated dewaxing buffer reagent solutions are shown below Tables 4-6.

TABLE 4

Dewax Buffer - Low pH

| Component | Volume (ml) | Percent |
|---|---|---|
| Citrate Buffer Concentrate | 15 | 15% |
| DI Water | 48 | 48% |
| PEG 200 | 22 | 22% |
| Triton X100 | 7.5 | 7.5% |
| THFA | 7.5 | 7.5% |
| Total | 100 | 100.00% |

TABLE 5

Dewax Buffer - Medium pH

| Component | Volume (ml) | Percent |
|---|---|---|
| EDTA-HEPES Buffer Concentrate | 15 | 15% |
| DI Water | 48 | 48% |
| PEG 200 | 22 | 22% |
| Triton X100 | 7.5 | 7.5% |
| THFA | 7.5 | 7.5% |
| Total | 100 | 100.00% |

TABLE 6

Dewax Buffer - High pH

| Component | Volume (ml) | Percent |
|---|---|---|
| Tris-EDTA Buffer Concentrate | 15 | 15% |
| DI Water | 48 | 48% |
| PEG 200 | 22 | 22% |
| Triton X100 | 7.5 | 7.5% |
| THFA | 7.5 | 7.5% |
| Total | 100 | 100.00% |

Example 3

Dewax Buffers

Paraffin Solubility Testing

The purpose of this set of tests is to understand the role that tetrahydrofuryl alcohol and polyethylene glycol have on the solubility of paraffin in an aqueous buffer solution. The Dewax HIER buffers have been formulated such that paraffin is partially dissolved during the HIER process. The paraffin is removed from vertically immersed slides during HIER in the PT Module. Upon cooling, the paraffin partially re-precipitates, but to a much lesser degree than in with other known dewaxing buffers.

Because the PT Module requires slides to be in a vertical orientation, it is required that paraffin become completely dissolved into the buffer during the higher heating steps of the HIER process (that is, above 85 degrees C.). During this high heating phase, the paraffin melts away from the slide. If there is no additive in the buffer solution to encourage solubility of the paraffin, it will simply pool at the top surface of the buffer, like oil on water (or olive oil on vinegar).

After the buffers have come to cooling temperatures, approximately 75 to 85 degrees C., when the slides can be removed from the HIER buffers, the buffer solution may recoat the slides if there are no additives to encourage paraffin solubility. Using additives such as polyethylene glycol 200 (PEG 200) and methyl tetrahydrofuryl alcohol (THFA), we have been able to partially dissolve paraffin during the HIER process. These experiments are designed to illustrate how these two additives behave in an aqueous buffer solution with paraffin (Histoplast LP) at various temperatures.

Expected Results: It is expected that the results will illustrate that neither THFA, nor PEG 200, act alone in the partial paraffin solubility property of the dewaxing buffer. Rather, it is expected that the results will show that the two additives work together to create the partial paraffin solubility character of the dewaxing buffer.

Experimental Design:
Buffers:
D HIER L1—buffer containing citrate buffer, 1.5 vol % PEG 200, 0.5 vol % Triton X100, 0.5 vol % THFA, and ~97 vol % DI water.

D HIER L2: same as L1, except the PEG 200 was removed & replaced with DI water.

D HIER L3: same as L1, except the THFA was removed & replaced with DI water.

HIER L: standard citrate buffer for HIER containing no PEG 200 or THFA.

Dako Envision Flex Low pH (Red): competitor dewaxing buffer

Five grams of paraffin was placed in 100 ml of each of the buffers. The solutions were heated to 58 degrees C. with constant stirring. The relative percentage of paraffin that was dissolved was observed at 58 degrees C. The working solutions were allowed to continue to heat with constant stirring, and the temperature was recorded when the paraffin was completely dissolved. Thereafter, the solutions were removed from heat and allowed to come to 55 degrees C. The solutions were filtered at 55 degrees C. and the residue collected on the filter paper was massed. The mass filtered out was subtracted from the mass originally placed in each of the working solutions. The difference is the mass of paraffin that was in solution at 55 degrees C.

Observations:

1. During the heating phase of the experiment, it was noticed that D HIER L1 and D HIER L2 make complete suspensions with the molten paraffin. That is, the solution was turbid, frothy, and did not show any separation from the aqueous working solution.

2. During the heating phase of the experiment, it was noticed that D HIER L3 displayed an oily layer on top of the aqueous buffer. This oily layer was clear and colorless. The aqueous solution was clear & tinted light orange (consistent with the coloration of the parent buffer). The aqueous buffer was not at all turbid and showed no frothing.

3. During the heating phase of the experiment, it was noticed that HIER L buffer displayed a significant oily layer that was clear and colorless. The aqueous buffer solution was also clear and colorless, and showed no turbidity or frothing.

4. During the heating phase of the experiment, it was noticed that Dako Envision Flex Red buffer displayed a significant oily layer on top of the aqueous buffer. The oily layer was clear & colorless. The aqueous buffer layer was clear and tinted light red, consistent with the color of the parent buffer.

5. D HIER L1, L2, and L3 each dissolved (i.e., melted) 90% of the paraffin at 58 degrees C. HIER L buffer and Dako Flex buffers only showed 40% and 60% dissolution, respectively.

6. D HIER L1 and L2 each showed 100% paraffin dissolution at 62 degrees C.

7. D HIER L3 showed 100% paraffin dissolution at 66 degrees C.

8. HIER L showed complete dissolution at 79 degrees C.

9. Dako Flex Red showed complete dissolution at 68 degrees C.

10. D HIER L1 retained 0.3582 g of paraffin (7%) in solution at 55 degrees C.

11. D HIER L2 retained 0.5580 g of paraffin (11%) in solution at 55 degrees C.

12. D HIER L3 retained 0.1627 g of paraffin (3%) in solution at 55 degrees C.

13. HIER L retained 0.2528 g of paraffin (5%) in solution at 55 degrees C.

14. Dako Red retained 0.2786 g of paraffin (6%) in solution at 55 degrees C.

15. D HIER L1 retained 0.2337 g of paraffin between 55 degrees C. and 24 degrees C. (5%)

16. D HIER L2 retained 0.2570 g of paraffin between 55 degrees C. and 24 degrees C. (5%)

17. D HIER L3 retained 0.1010 g of paraffin between 55 degrees C. and 24 degrees C. (2%)

18. HIER L retained 0 g of paraffin between 55 degrees C. and 24 degrees C. (0%)

19. Dako Flex Red retained 0 g of paraffin between 55 degrees C. and 24 degrees C. (0%)

Final Observations:

The above results show qualitative and quantitative evidence that THFA, contained within the Dewax buffer formulation, makes an important difference in causing the partial solubility behavior of paraffin wax.

Without THFA, none of the dewax formulations, competitor formulation (Dako Envision Flex Red), or routine HIER buffer were capable of solublizing paraffin, even at high temperatures. The paraffin wax merely melted & formed a clear, colorless phase on top of the aqueous phase. These phases were unable to be mixed, even temporarily, at any temperature.

THFA allows the molten paraffin wax to become solubilized within the buffer at warm temperatures (approximately 52-62 degrees C.). A turbid solution is formed, without any trace of separated phases or layers.

The paraffin wax dissolves into the Dewax solutions (with THFA) at lower temperatures than the Dewax buffer lacking THFA or the Dako buffer or the control HIER buffer.

Much more mass of the paraffin wax remains in solution with Dewax L containing THFA (2.5 times as much) than in Dewax L without THFA. The control and competitor (HIER L and Dako Flex Red) did not retain any paraffin wax in this temperature range; all paraffin wax was filtered out at the higher temperature of 55 degrees C.

Dewax Buffer that contains THFA causes a partial solubility of paraffin at higher temperatures (55 degrees C. and higher) and also maintains partial solubility of some of this paraffin between 24 degrees C. and 54 degrees C. It isn't until the buffer reaches room temperature that the paraffin wax completely falls out of solution. This is unlike the control buffer (a buffer not formulated to deparaffinize) and the competitor buffer (formulated to remove paraffin, but by a horizontal slide mechanism).

Example 4

Dewaxing Buffers

Testing of Alternative Formulations

The formulations of several alternative dewaxing buffer working solutions are shown below Table 7.

TABLE 7

|  | 2 L Batches | Percent | 1 L | 100 ml |
|---|---|---|---|---|
| Test Formula 1A |  |  |  |  |
| DI Water | 1408 ml | 0.704 | 704 ml | 70.4 ml |
| Citric Acid Monohydrate | 147.46 g | 0.07373 | 73.73 g | 7.373 g |
| 10N Sodium Hydroxide | 192 ml | 0.0737 | 73.7 ml | 7.37 ml |
| Mineral Oil | 200 ml | 0.1 | 100 ml | 10 ml |
| Tween 20 | 200 ml | 0.1 | 100 ml | 10 ml |
| Test Formula 1B |  |  |  |  |
| DI Water | 1408 ml | 0.704 | 704 ml | 70.4 ml |
| Citric Acid Monohydrate | 147.46 g | 0.07373 | 73.73 g | 7.373 g |
| 10N Sodium Hydroxide | 192 ml | 0.0737 | 73.7 ml | 7.37 ml |
| Mineral Oil | 200 ml | 0.1 | 100 ml | 10 ml |
| Triton X100 | 200 ml | 0.1 | 100 ml | 10 ml |
| Test Formula |  |  |  |  |

TABLE 7-continued

1C

| Component | | | | |
|---|---|---|---|---|
| DI water | 1731.2 ml | 0.8656 | 865.6 ml | 86.56 ml |
| Citric Acid Monohydrate | 147.46 g | 0.07373 | 73.73 g | 7.373 g |
| 10N Sodium Hydroxide | 192 ml | 0.096 | 96 ml | 9.6 ml |
| Tween 20 | 76.8 ml | 0.001 | 1 ml | 0.1 ml |
| Diethanolamine | 100 ml | 0.050 | 50 ml | 5 ml |

Test Formula 1D

| Component | | | | |
|---|---|---|---|---|
| DI water | 1731.2 ml | 0.8656 | 865.6 ml | 86.56 ml |
| Citric Acid Monohydrate | 147.46 g | 0.07373 | 73.73 g | 7.373 g |
| 10N Sodium Hydroxide | 192 ml | 0.096 | 96 ml | 9.6 ml |
| Tween 20 | 76.8 ml | 0.001 | 1 ml | 0.1 ml |
| me-THF | 10 ml | 0.005 | 5 ml | 0.5 ml |

Test Formula 1E

| Component | | | | |
|---|---|---|---|---|
| DI water | 1731.2 ml | 0.8656 | 865.6 ml | 86.56 ml |
| Citric Acid Monohydrate | 147.46 g | 0.07373 | 73.73 g | 7.373 g |
| 10N Sodium Hydroxide | 192 ml | 0.096 | 96 ml | 9.6 ml |
| Tween 20 | 76.8 ml | 0.001 | 1 ml | 0.1 ml |
| Diethanolamine | 100 ml | 0.050 | 50 ml | 5 ml |
| me-THF | 10 ml | 0.005 | 5 ml | 0.5 ml |

Test Formula 1F

| Component | | | | |
|---|---|---|---|---|
| DI water | 1731.2 ml | 0.8656 | 865.6 ml | 86.56 ml |
| Citric Acid Monohydrate | 147.46 g | 0.07373 | 73.73 g | 7.373 g |
| 10N Sodium Hydroxide | 192 ml | 0.096 | 96 ml | 9.6 ml |
| Tween 20 | 76.8 ml | 0.001 | 1 ml | 0.1 ml |
| Diethanolamine | 200 ml | 0.100 | 100 ml | 10 ml |

Test Formula 1G-1

| Component | | | | |
|---|---|---|---|---|
| DI water | 1731.2 ml | 0.8656 | 865.6 ml | 86.56 ml |
| Citric Acid Monohydrate | 147.46 g | 0.07373 | 73.73 g | 7.373 g |
| 10N Sodium Hydroxide | 192 ml | 0.096 | 96 ml | 9.6 ml |
| Tween 20 | 76.8 ml | 0.001 | 1 ml | 0.1 ml |
| me-THF | 20 ml | 0.010 | 10 ml | 1 ml |

Test Formula 1G-2

| Component | 20 mL Batches | 2 L | 1 L | 100 ml |
|---|---|---|---|---|
| DI Water | 17.2 ml | 1720 ml | 860 ml | 86 ml |
| Citrate | 0.4632 g | 46.32 g | 23.16 g | 0.2316 g |
| Sodium Citrate Dihydrate | 5.2 g | 520 g | 260 g | 2.6 g |
| Proclin 950 | 0.02 g | 2 ml | 1 ml | 0.01 ml |
| Red Food Coloring | 0.003 ml | 0.30 ml | 0.15 ml | 0.0015 ml |
| Yellow Food Coloring | 0.006 ml | 0.60 ml | 0.30 ml | 0.003 ml |
| me-THF | 0.2 ml | 20 ml | 10 ml | 1 ml |

Test Formula 1H

| Component | | | | |
|---|---|---|---|---|
| DI Water | 17.2 ml | 1720 ml | 860 ml | 86 ml |
| Citrate | 0.4632 g | 46.32 g | 23.16 g | 0.2316 g |
| Sodium Citrate Dihydrate | 5.2 g | 520 g | 260 g | 2.6 g |
| Proclin 950 | 0.02 g | 2 ml | 1 ml | 0.01 ml |
| Red Food Coloring | 0.003 ml | 0.30 ml | 0.15 ml | 0.0015 ml |
| Yellow Food Coloring | 0.006 ml | 0.60 ml | 0.30 ml | 0.003 ml |
| Diethanolamine | 5 ml | 385 | 192.5 | 19.25 |
| Propylene glycol | 1 ml | 77 | 38.5 | 3.85 |

Test Formula 1I

| Component | 100 mL Batches | 2 L | 1 L |
|---|---|---|---|
| DI Water | 12.9 ml | 258 ml | 129 ml |
| Citrate | 0.345 g | 6.9 g | 3.45 g |
| Sodium Citrate Dihydrate | 3.9 g | 78 g | 39 g |
| Proclin 950 | 0.015 ml | 0.30 ml | 0.15 ml |
| Red Food Coloring | 0.0015 ml | 0.30 ml | 0.15 ml |
| Yellow Food Coloring | 0.003 ml | 0.60 ml | 0.30 ml |
| DI Water | 48 ml | 960 | 480 |
| PEG200 | 22 ml | 440 | 220 |
| Triton X100 | 7.5 ml | 150 | 75 |
| THFA | 7.5 ml | 150 | 75 |

Test Protocol

Except where noted, three (3) slides were tested in each buffer formulation. Prior to buffer treatment, the slides were incubated in a lab oven at 70° C. for 20 minutes In order to test each buffer, the slides were removed from the oven and transferred to a PT Module filled with buffer, which was preheated to 85° C. The PT Module was then heated to 97° C. and the slides were incubated at that temperature for 20 minutes for dewaxing and epitope retrieval. After dewaxing, the slides were processed according to standard protocols.

Results

Formula 1A yielded a milky white solution when it was mixed up. The dewaxing behavior of Formula 1A was not tested.

Formula 1B—Results were inadequate to make a determination as to the effectiveness of the formulation.

Formula 1C—Three slides were tested with this formulation. The buffer deparaffinized 2 of 3 slides well, IHC good on the 2 that were well-deparaffinized.

Formula 1D—Three slides were tested with this formulation. The buffer deparaffinized 2 of 3 slides well, IHC good on the 2 that were well-deparaffinized Formula 1E—Three slides were tested with this formulation. The buffer deparaffinized 3 slides well, but loss of some tissue after HIER on PTM, lost peptides.

Formula 1F—Three slides were tested with this formulation. The buffer deparaffinized all 3 slides well, but loss of some tissue after HIER on PTM, lost peptides.

Formula 1G-1 and 1G-2—Three slides were tested with each of these formulations. The buffer deparaffinized each of the slides well, no loss of tissue, no loss of peptides (spots show good AR), excellent IHC results.

Formula 1H—Three slides were tested with this formulation. The buffer deparaffinized 3 slides well, but there was some loss of tissue and some loss of peptides.

Formula 1I—Three slides were tested with this formulation. The buffer deparaffinized 3 slides well, no loss of tissue, no loss of peptides (spots show good AR), excellent IHC results.

SUMMARY

Formulas 1A and 1B performed unacceptably because rather than create a aqueous solution with synergistic properties capable of partially solublizing paraffin, Formulas 1A and 1B formed suspensions within themselves and lacked any capacity to solubilize paraffin.

Formulas 1C and 1D showed some promise as to the partial solubility of paraffin as well as IHC signal, however, the performance was inconsistent. Some slides did not deparaffinize well while others seemed to be well deparaffinized.

Formulas 1E, 1F, and 1H were too aggressive. While they performed exceptionally for the paraffin solubility, the chemical treatment was much too harsh on the tissue sections. This is evidenced by the fact that some tissue sections fell off the slides and some peptides were lost. This is generally unacceptable.

Formulas 1G-1, 1G-2, and 1I illustrated excellence in paraffin solubility, excellence in IHC signal, and consistency in performance. The success of these formulations was attributed to the active ingredients of either me-THF or THFA. These formulas were moved into verification and validation ("V&V") testing. In V&V testing, not only were the performance and consistency of Formulas 1G and 1I further illustrated, but the formulations containing THFA and PEG200 were shown to be an improvement over the formula containing me-THF, due to the minimal to zero odor of THFA-containing buffers. In addition, THFA is less volatile relative to me-THF, which means that the solvent does not readily evaporate from the buffer under operating temperatures and the performance of the buffer was more consistent over time. That is, because the amount of THFA in the buffer did not change appreciably during dewaxing and HIER procedures, the ability of the buffer to solublize paraffin did not degrade appreciably over time and, in particular, during one or more dewaxing and HIER runs.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dewaxing buffer, consisting of:
   a buffering agent;
   an organic solvent selected from the group consisting of: tetrahydrofurfuryl alcohol and methyl tetrahydrofuran;
   at least one of PEG 200, PEG 300, PEG 400, or PEG 600; and
   water.

2. The dewaxing buffer of claim 1, wherein the organic solvent has a boiling point greater than 150° C.

3. The dewaxing buffer of claim 1, wherein the at least one of PEG 200, PEG 300, PEG 400, or PEG 600 is included in an amount ranging from about 0.5 vol % to about 2 vol %.

4. The dewaxing buffer of claim 1, wherein the water comprises greater than 95 vol % of the dewaxing buffer.

5. A dewaxing buffer, consisting of:
   a buffering agent selected from the group consisting of citrate, EDTA-HEPES, and Tris-EDTA;
   tetrahydrofurfuryl alcohol in an amount ranging from 0.1 vol % to 0.75 vol %;
   polyethylene glycol 200 in an amount ranging from 0.5 vol % to 2 vol %;
   a surfactant in an amount of 0.1 vol % to 0.75 vol %, wherein the surfactant is selected from the group consisting of octyl phenol ethoxylate, polyoxyethylene (20) sorbitan monolaurate, and combinations thereof and
   water.

6. The dewaxing buffer of claim 1, wherein the buffering agent is selected from the group consisting of citrate, EDTA-HEPES, and Tris-EDTA.

7. A dewaxing buffer, consisting of:
   a buffering agent;
   an organic solvent selected from the group consisting of: tetrahydrofurfuryl alcohol and methyl tetrahydrofuran;
   at least one of PEG 200, PEG 300, PEG 400, or PEG 600;
   a surfactant; and
   water.

8. The dewaxing buffer of claim 7, wherein the surfactant is included in an amount ranging from about 0.2 vol % to about 4 vol %.

9. The dewaxing buffer of claim 7, wherein the surfactant is selected from the group consisting of an anionic surfactant, a cationic surfactant, a zwitterionic surfactant, a nonionic surfactant, and combinations thereof.

* * * * *